(12) United States Patent
Fishbein

(10) Patent No.: US 7,632,276 B2
(45) Date of Patent: Dec. 15, 2009

(54) MINIMALLY INVASIVE COLLAPSIBLE SURGICAL REAMER

(75) Inventor: Meyer Fishbein, Westestborough, MA (US)

(73) Assignee: Greatbatch Medical SA, Orvin (CH)

( * ) Notice: Subject to any disclaimer, the term of this patent is extended or adjusted under 35 U.S.C. 154(b) by 777 days.

(21) Appl. No.: 10/902,692

(22) Filed: Jul. 29, 2004

(65) Prior Publication Data

US 2006/0025774 A1 Feb. 2, 2006

(51) Int. Cl.
*A61B 17/00* (2006.01)
(52) U.S. Cl. .............................. 606/80; 606/79; 606/81
(58) Field of Classification Search ............. 606/79–81, 606/91; 408/20, 158, 159, 180, 190; 175/284, 175/285
See application file for complete search history.

(56) References Cited

U.S. PATENT DOCUMENTS

| 59,631 | A | * | 11/1866 | Nottingham et al. | ........ | 175/285 |
| 2,654,575 | A | * | 10/1953 | Kammerer | ................. | 175/266 |
| 3,702,811 | A | | 11/1972 | Fishbein | | |
| 5,178,625 | A | * | 1/1993 | Groshong | ................... | 606/159 |
| 5,658,290 | A | | 8/1997 | Lechot | | |
| 6,224,604 | B1 | * | 5/2001 | Suddaby | ...................... | 606/80 |
| 6,264,647 | B1 | | 7/2001 | Lechot | | |
| 6,918,914 | B2 | * | 7/2005 | Bauer | .......................... | 606/81 |
| 2006/0217730 | A1 | * | 9/2006 | Termanini | ..................... | 606/81 |

FOREIGN PATENT DOCUMENTS

WO WO2006/127904 11/2006

* cited by examiner

*Primary Examiner*—Thomas C Barrett
*Assistant Examiner*—Andrew Yang
(74) *Attorney, Agent, or Firm*—Moetteli & Associés SàRL

(57) ABSTRACT

A preferred acetabular reamer is disclosed for cutting a bone socket, defining an apex and rotatable about a drive axis. The reamer has a domed support portion adjacent the apex and a plurality of cutting members, which may be of the cheese grater or bladed type, each pivotally mounted on the support portion. A hub structure including a sleeve portion is movable along the axis toward and away from the apex. A plurality of spokes operatively connects the cutting members and the hub, respectively. Actuation of the hub, in turn, radially collapses the spokes causing the cutting members to assume an insertion profile during passage of the reamer through a surgical incision, and then radially expands the spokes causing the cutting members to assume a larger, cutting profile while reaming the bone socket. A surgical kit and method employing the inventive reamer are also disclosed.

23 Claims, 10 Drawing Sheets

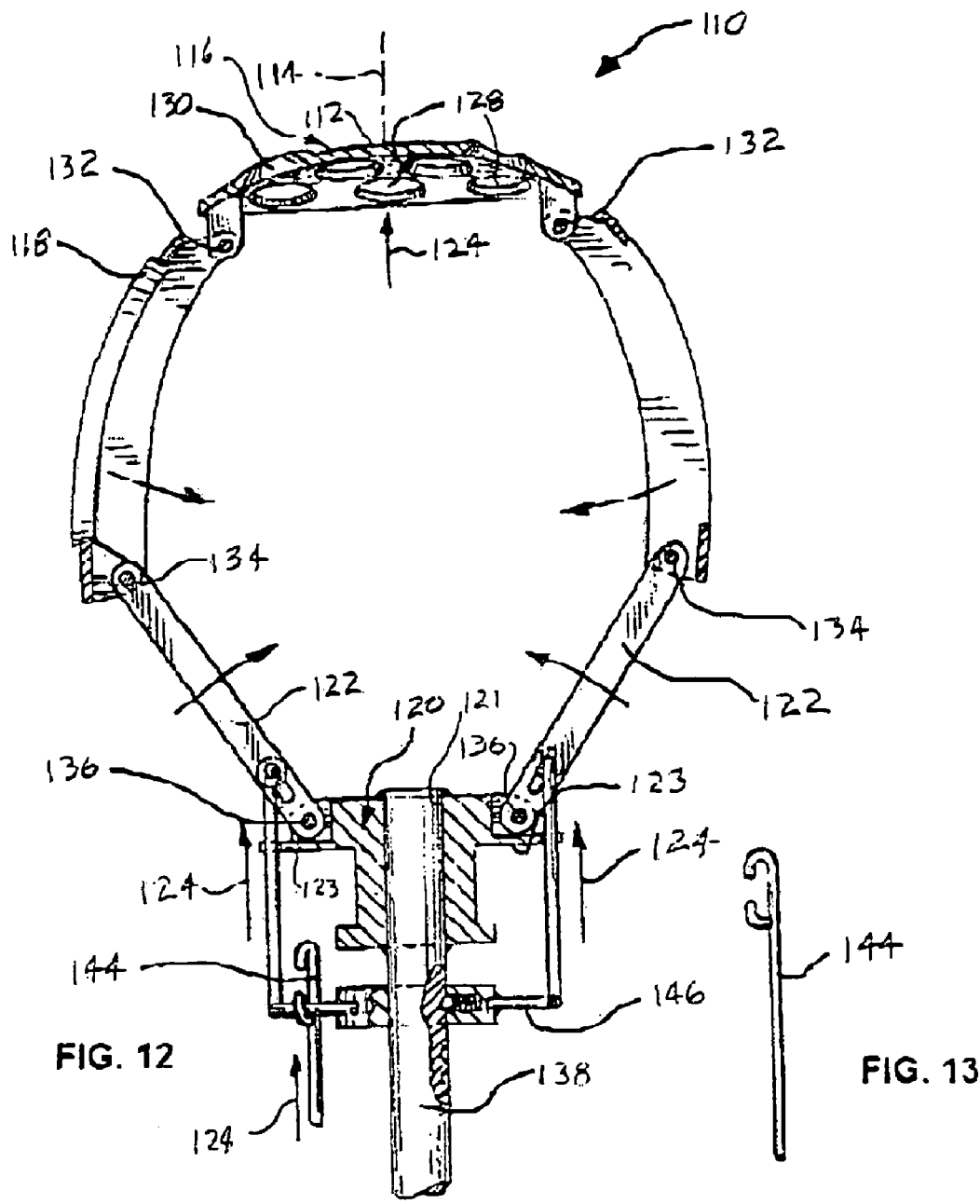

MINIMALLY INVASIVE COLLAPSIBLE SURGICAL REAMER

TECHNICAL FIELD

This invention generally relates to surgical reamers, particularly those used for cutting a domed-shaped cavity in a bone, more particularly in an acetabulum, to prepare the bone surface for receiving an implantable prosthesis.

BACKGROUND OF THE INVENTION

An objective of orthopedic surgery is to continue developing improved devices and methods that are less invasive to the patient. These efforts include minimizing the incision required to employ surgical instrumentation in the preparation of a bone cavity or socket to receive an implant in, e.g., an acetabular reaming procedure. A way to minimize the incision is to optimize the geometry that the reamer presents to the incision, characterized herein as its "static insertion profile area". By simplifying the surgical steps required, the reamer design can further lessen total inter-operative time and hence decrease the risks generally associated with longer surgical procedures.

Hollow domed acetabular reamers with hemispherical shapes have previously been disclosed, e.g., PCT/US99/05951 and U.S. Pat. Nos. 5,658,290 and 6,264,647, which are assembled to driving shafts for controlled rotation about a cut axis during the reaming operation. Such prior art acetabular reamers present a circular static insertion profile area (with no straight sides) to the surgical incision, generating a circular dynamic profile area upon rotation of the reamer in the bone socket. A cotyloid reamer is shown in U.S. Pat. No. 6,106,536 having a much different i.e., lop-sided construction compared to the prior acetabular reamers. This cotyloid reamer presents a semi-circular static insertion profile area (i.e., one straight side) to the surgical incision, which is less than the circular dynamic profile area generated upon rotation of the reamer in the bone.

Another objective of orthopedic surgery is to develop instrumentation that is more handily and efficiently used while accurately maintaining a precise cut of the bone socket, in order to minimize inter-operative time. The above-mentioned patent documents also discuss various alternative connections by which their reamers may be assembled to a handle, such assemblies including alignment structures on the reamer and handle allowing controlled rotation of the reamer in the bone socket further to a precision cut.

PCT US02/21310 discloses a reamer that seeks to reduce the static insertion profile area of the reamer to minimize the size of the surgical incision, while providing a precise cut of the desired bone cavity. This reamer employs connections between the reamer and shaft that are designed to perform with a less invasive reamer geometry. These connections function with different handles having a variety of bayonet or other assembly connections, regardless of reamer geometry. This reamer further provides a tool-shaft connection to either a conventional or a less invasive geometry, which allows bone and other organic matter trapped in the reamer, to be removed effectively. The entire contents of the aforesaid PCT/US02/21310 are expressly incorporated by reference herein and relied-upon.

The above-mentioned patent documents have respectively discussed reamers with static insertion geometries that generate dynamic cutting profiles by rotation of the reamer. Generally, there is otherwise no radial expansion or collapsing of the static structure itself.

U.S. Pat. No. 3,702,611 issued to the present inventor discloses a reamer having radially expandable blades that are actuated by cam elements to expand the cutters progressively in response to axial thrust exerted on the drive shaft by the surgeon with the reamer head seated in the acetabulum. A spring is used to contract the cutters when the reaming operation is stopped. The inventor's purpose was to provide radially expandable blades to accurately bottom-out the reamer by using the axial movement (by the surgeon) and radial expansion (of the blades) in combination with one another. However, the cutting structure described by the '611 patent contemplates the use of bladed cutting members rather than a domed apex and/or cutting panels each presenting multiple discrete cutting sites, e.g., of the "cheese grater" type employed by other approaches already discussed above.

Accordingly, it would still be desirable to have a reamer (more particularly an acetabular reamer) that is radially collapsible during passage through a surgical incision then expandable for reaming the bone socket and for collection of debris.

It would be further desirable to provide a hollow dome-shaped reamer having the immediately aforementioned objects, in order to improve accuracy of cut when bottoming-out the reamer in a bone socket, as well as improve the collection of debris.

SUMMARY OF THE INVENTION

According to one aspect of the present invention, there is provided a surgical reamer for cutting a bone socket, defining an apex and rotatable about a drive axis. The reamer has a support portion aligned with the axis and a plurality of cutting members each mounted on the support portion. A plurality of spokes is operatively connected to the cutting members, respectively. Actuation of the spokes, in turn, radially collapses the cutting members causing the reamer to assume a less invasive insertion profile during passage of the reamer through a surgical incision, and then radially expands the cutting members causing the reamer to assume a larger, cutting profile while reaming the bone socket. Preferably, the cutting members may form solid panels having discrete open cutting sites with raised teeth or may form arcuate blades. Also preferably, the support portion defines a hollow concave domed shape, more preferably the domed support portion has discrete open cutting sites with raised teeth for passage of debris. Also preferably, the cutting members are pivotally connected to the domed portion by hinges. Also preferably, the reamer has a releasable locking mechanism that maintains the cutting members in an expanded state for reaming or in a collapsed state for passage through the incision.

According to a preferred embodiment of the present invention, there is provided a surgical reamer for cutting a bone socket, defining a drive axis and an apex. The reamer has a hollow, concave domed portion and a plurality of cutting panels each hingedly supported by the domed portion. Pluralities of open cutting sites are located on the panels, respectively, including raised teeth at the cutting sites, for passage of debris. The reamer has a hub movable along the axis toward and away from the apex, and has a plurality of spokes extending between the cutting panels and the hub, respectively. Actuation of the hub radially collapses the spokes causing the cutting panels and in turn the reamer to assume a less invasive insertion profile during passage of the reamer through a surgical incision, and then radially expands the cutting panels to assume a larger, cutting profile while reaming the bone socket.

According to another preferred embodiment, there is provided a surgical reamer for cutting a bone socket. The reamer has a collapsible cutting structure rotatable about a drive axis, with an apex having a domed support portion including a plurality of bladed cutting members respectively hinged about the domed portion. A plurality of spokes extend between the cutting blades and the hub, respectively, the spokes being actuated to radially collapse the bladed cutting members to assume an insertion profile for passage through a surgical incision, and to radially expand the bladed cutting members for reaming the bone socket. The reamer defines an internal cavity for collection of debris. In a preferred embodiment, a plurality of hinges operatively connects the bladed cutting members to the hub.

According to a second aspect of the present invention, there is provided a surgical kit for cutting a bone socket. The kit includes a plurality of reamers having an array of sizes corresponding to the needs of individual patients. Each reamer size has a support portion that is preferably a hollow, concave domed shape and defines a drive axis and an apex, with a shaft preferably extending along the drive axis. Each reamer has a plurality of cutting members that preferably are pivotally supported by the domed portion, a hub structure including a sleeve movable along the axis toward and away from the apex and a plurality of spokes extending between the cutting members and the hub, respectively. Actuation of the spokes radially collapses the cutting members causing the reamer to assume a less invasive insertion profile during passage of the reamer through a surgical incision, and then radially expands the cutting members to assume a larger, cutting profile while reaming the bone socket. The kit further includes a manual holder for grasping the reamer, including a quick-disconnect coupling for engaging and disengaging the reamer with a source of rotary power.

According to a third aspect of the present invention, there is provided a surgical method for cutting a bone socket in a patient. The method includes the steps of: providing a reamer defining an apex and a drive axis, the reamer having a support portion adjacent the apex, a plurality of cutting members each pivotally mounted on the support portion, a hub movable along the drive axis toward and away from the apex and a plurality of collapsible spokes operatively connecting the cutting members and the hub, respectively. Another step includes providing a manual holder coupled to a source of rotary power and releasably connecting the reamer to the holder. Another step includes manually actuating the hub to radially collapse the spokes causing the cutting members to assume an insertion profile and passing the reamer through a surgical incision thence to the bone socket. Another step includes actuating the hub to radially expand the spokes causing the cutting members to assume a cutting profile larger than the insertion profile in the bone socket, then reaming the bone socket and collecting the surgical debris within the reamer. Another step includes actuating the hub to radially collapse the spokes causing the cutting members to assume the smaller, insertion profile and thence removing the reamer with its collected debris back through the incision.

Each of the above-listed aspects and preferred embodiments of the present invention is most preferably an acetabular reamer. It is further preferred that the reamer has a locking mechanism that alternately maintains the cutting members in a radially collapsed insertion profile and in a larger, radially expanded cutting profile, as assumed in the description elucidated above.

An advantage of the present invention is a reamer that necessitates a smaller sized surgical incision, compared with conventional reamers, as well as providing a minimally invasive tool contour that eases its surgical introduction through the incision into the bone cavity for reaming, all of the above while providing a precise shaping of the desired bone cavity.

Another advantage of a preferred reamer of the present invention is ease of extraction from the bone cavity through a relatively smaller surgical incision, via a minimally invasive tool contour.

Another advantage of a preferred reamer of the present invention is its ready access for removal of debris for collection.

Other objects and advantages will become apparent to those skilled in the art, upon reviewing the Figures of the Drawings, in conjunction with the Detailed Description set forth further below, wherein references to numerals corresponds to like references in the Drawings.

BRIEF DESCRIPTION OF THE DRAWINGS

FIG. 7 is a bottom view of the reamer of FIG. 6;

FIG. 12 is a sequential view of FIG. 11;

FIG. 13 is a perspective view of a preferred tool used by a surgeon to grasp the hub of FIGS. 10 and 12 to draw the hub axially toward and away from the apex of the reamer to radially collapse (FIGS. 10 and 12) and expand (FIG. 14) the cutting members (e.g., blades) according to the surgical method of the present invention;

DETAILED DESCRIPTION

Figure 1:
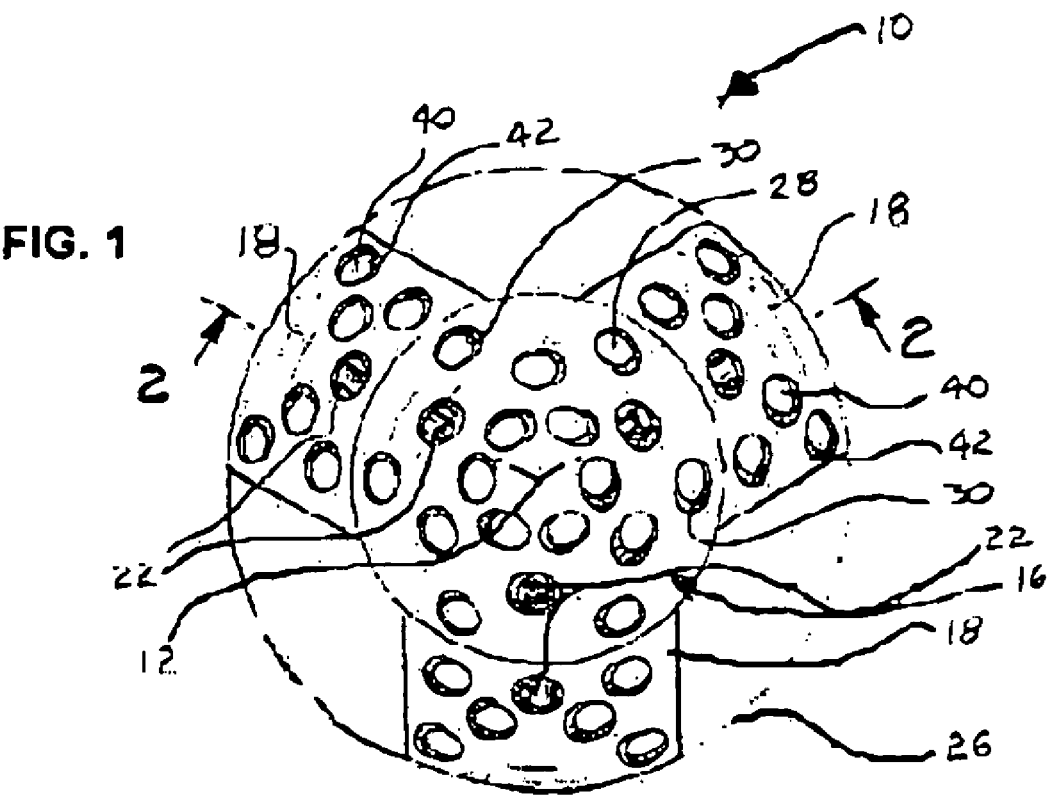
FIG. 1 is a top view of a preferred acetabular reamer of the present invention, showing cutting members embodied as solid panels provided with open cutting sites having raised teeth, the panels being hinged about a domed support member.
Figure 3:
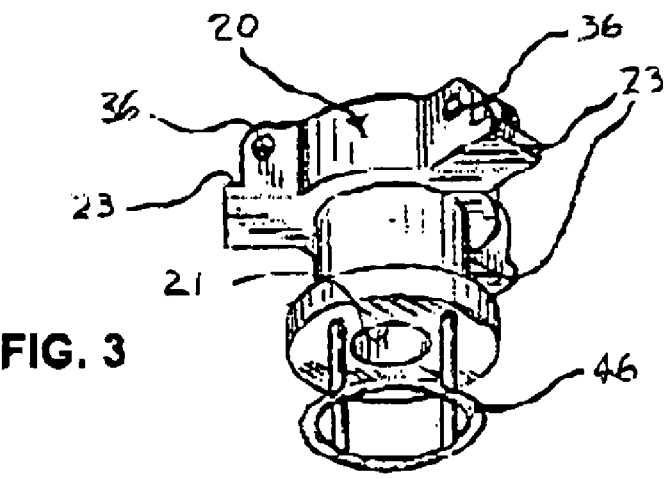
FIG. 3 is a perspective view of the preferred hub used to commonly connect each panel to the domed support member of FIGS. 1-2.
Figure 4:
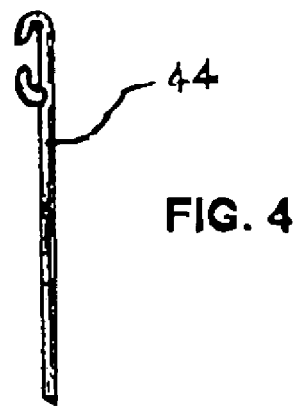
FIG. 4 is a perspective view of a preferred tool used by a surgeon to grasp the hub of FIGS. 2-3 and draw the hub axially toward and away from the apex of the reamer to radially collapse (FIG. 2) and expand (FIG. 6) the cutting members (e.g., panels) according to the surgical method of the present invention.
Figure 2:
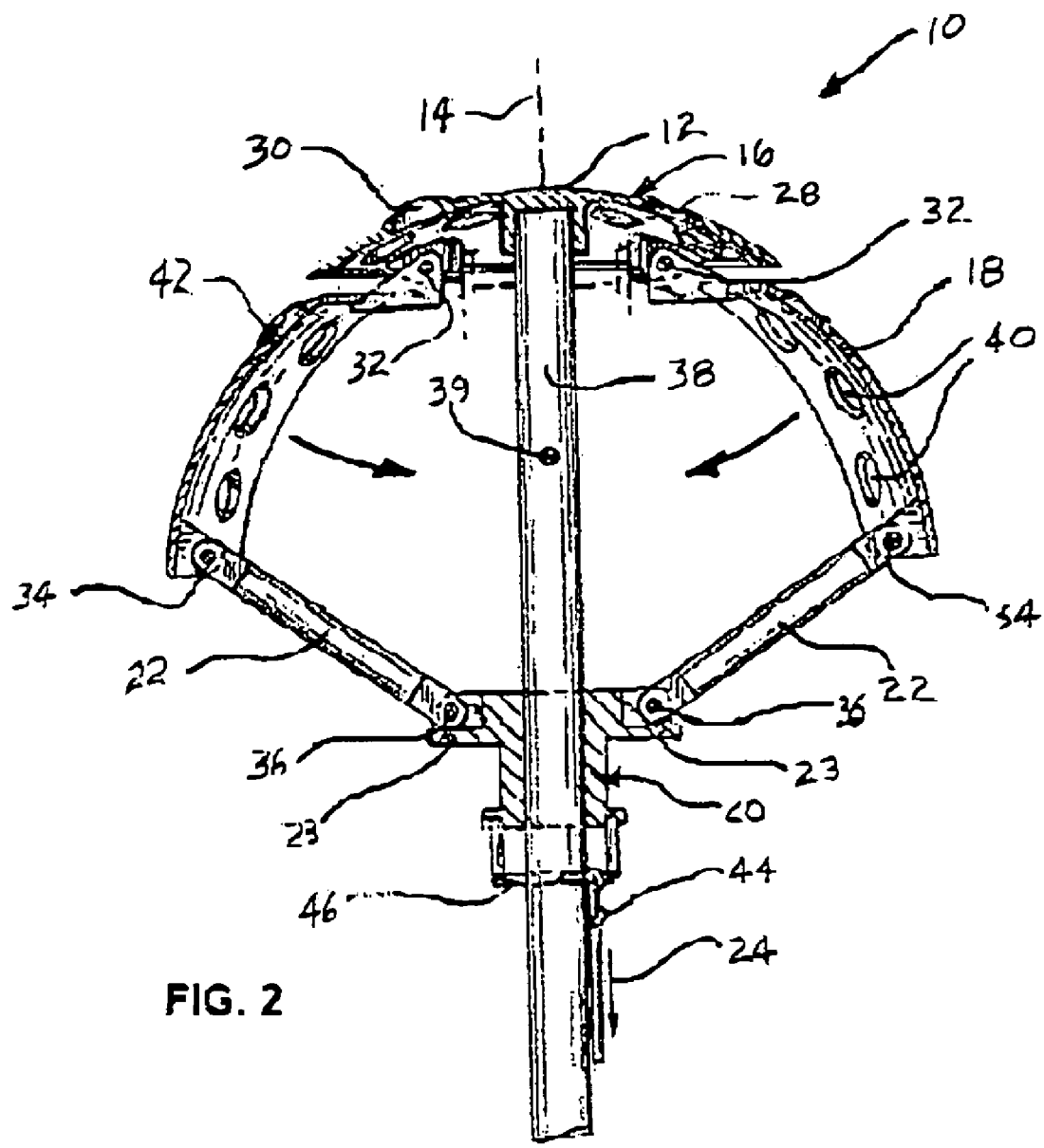
FIG. 2 is a sectional view taken substantially along the lines 2-2 of FIG. 1, showing the cutting panels in a partially collapsed state.
Figure 5:
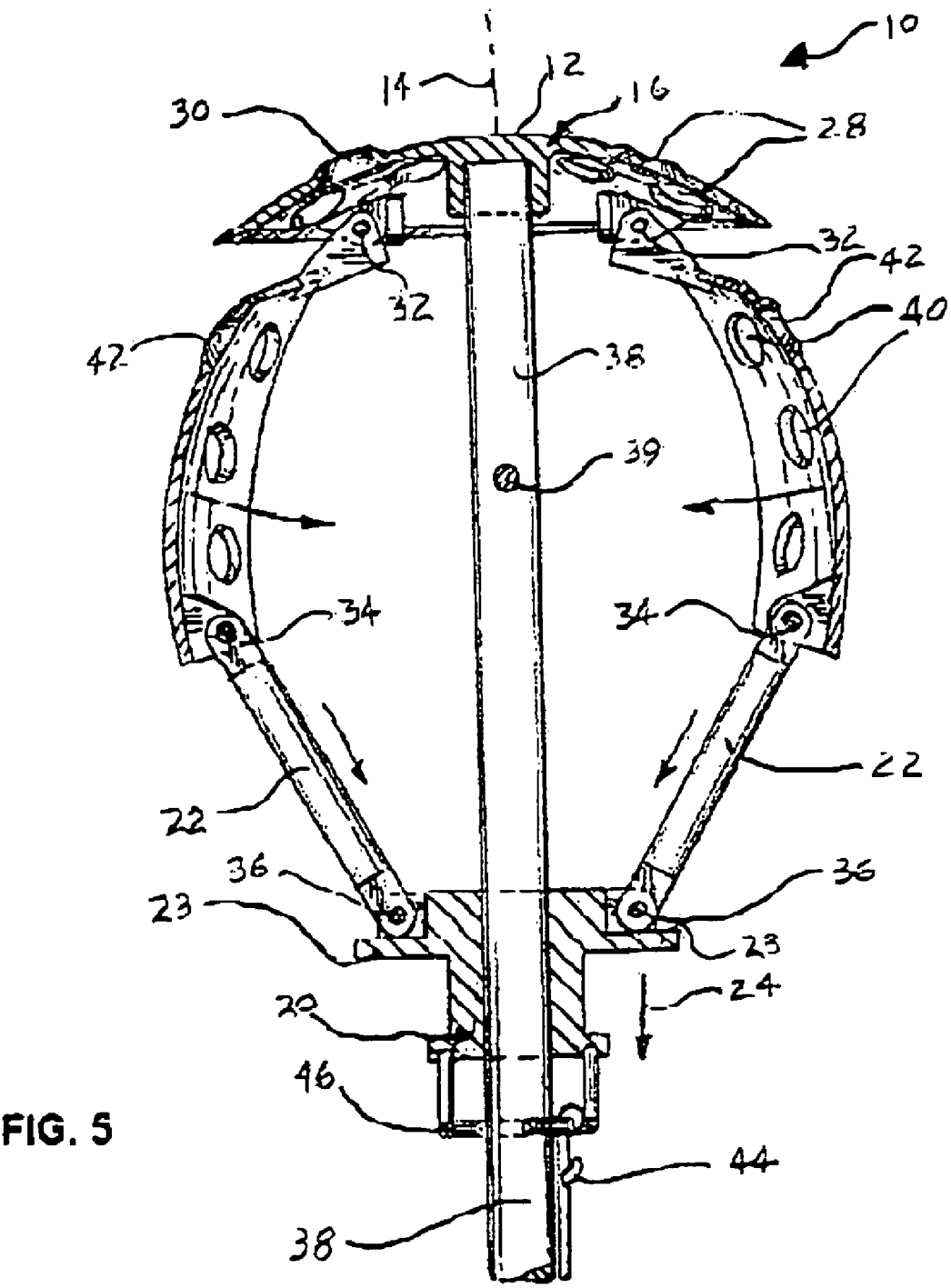
FIG. 5 is a sequential view of FIG. 2, showing the cutting members (i.e., panels) in a substantially collapsed state for introduction and removal of the reamer through the incision.
Figure 6:
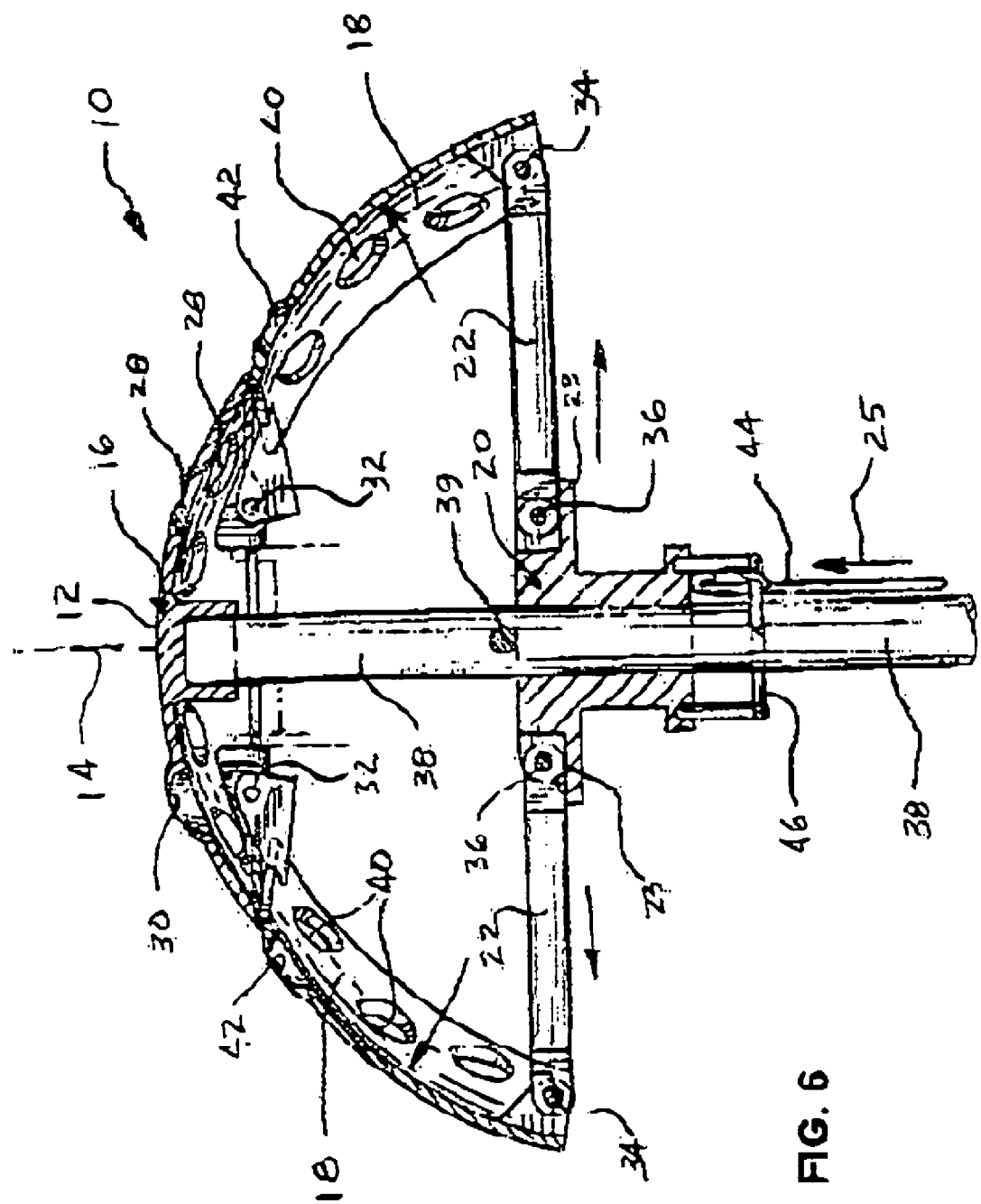
FIG. 6 is a sequential view of FIGS. 2 and 5, showing the cutting members (i.e., panels) in a state of full radial expansion for reaming a bone socket.
Figure 8:
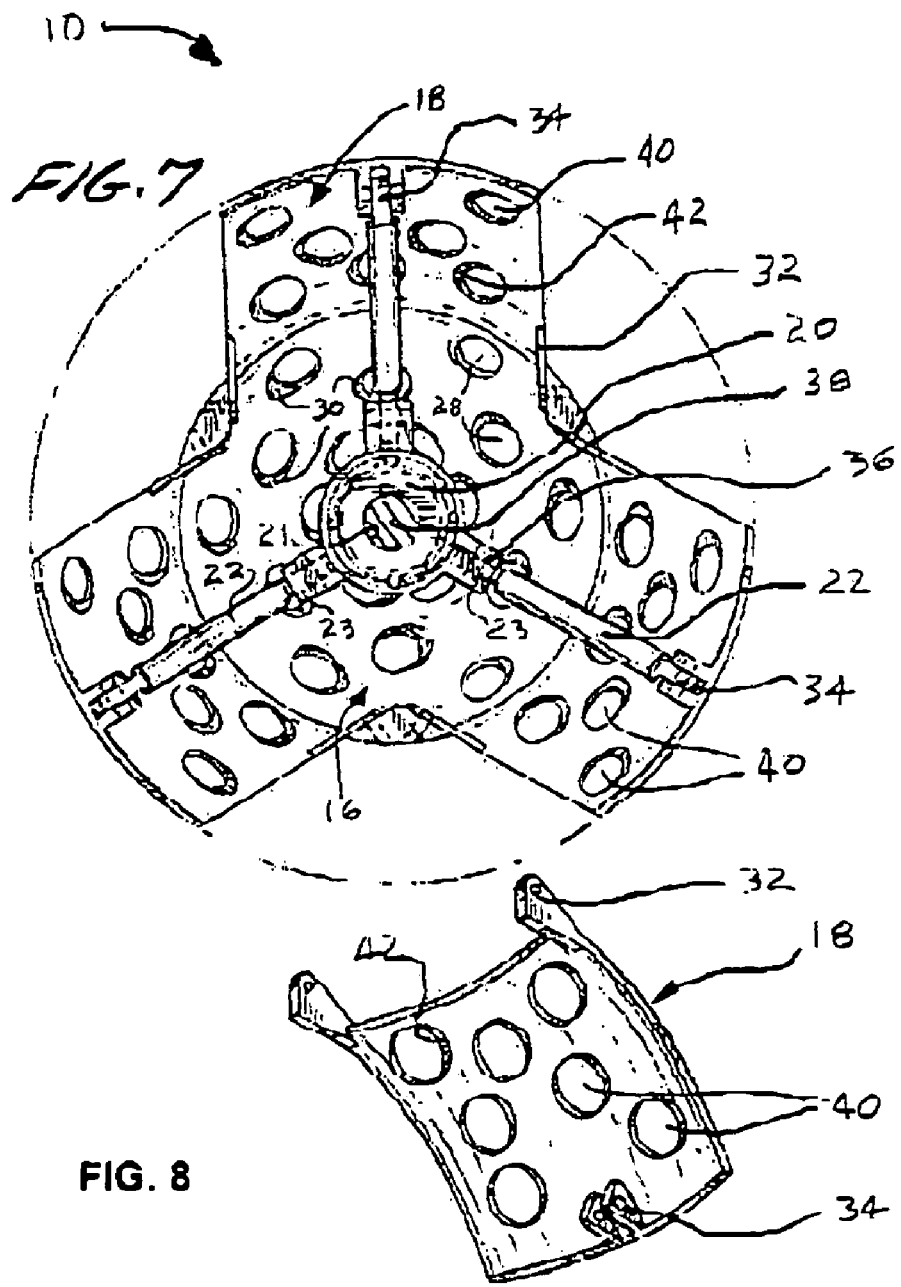
FIG. 8 is a perspective view of a representative preferred cutting panel depicted by FIGS. 1-2 and 5-7.
Figure 9:
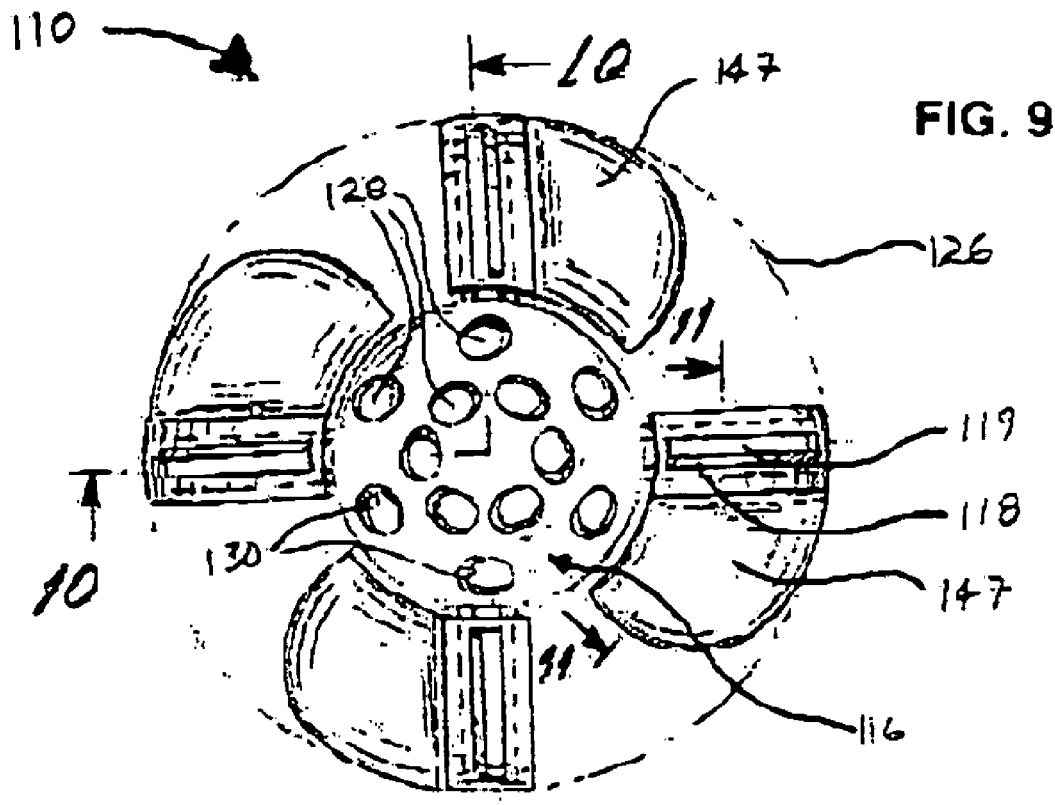
FIG. 9 is a top view of another preferred acetabular reamer of the present invention, showing a plurality of bladed cutting members.
Figure 11:
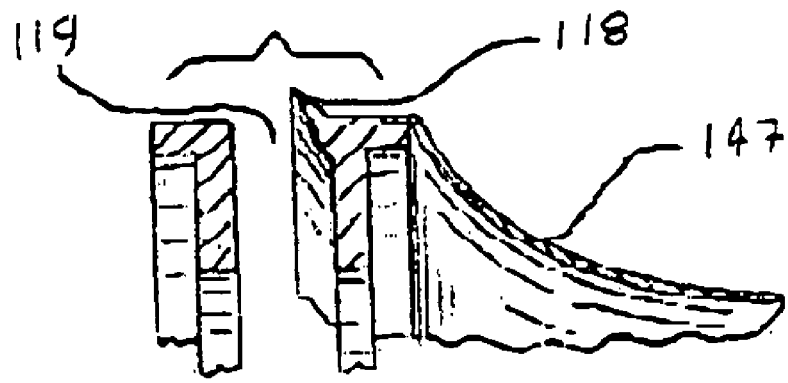
FIG. 11 is a partial sectional view taken substantially along lines 11-11 of FIG. 9.
Figure 10:
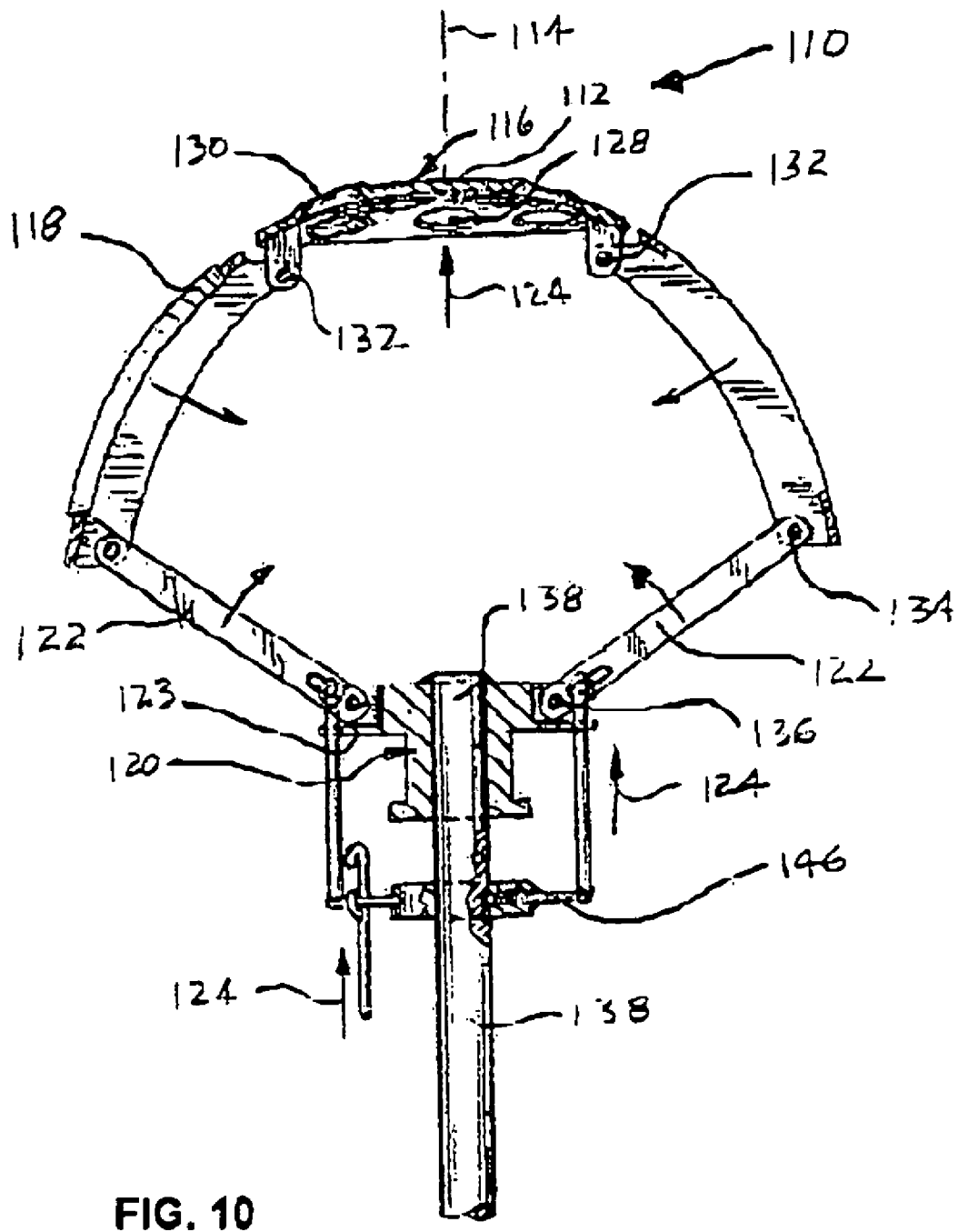
FIG. 10 is a partial sectional view taken substantially along lines 10-10 of FIG. 9, showing the reamer in a partially collapsed state.
Figure 14:
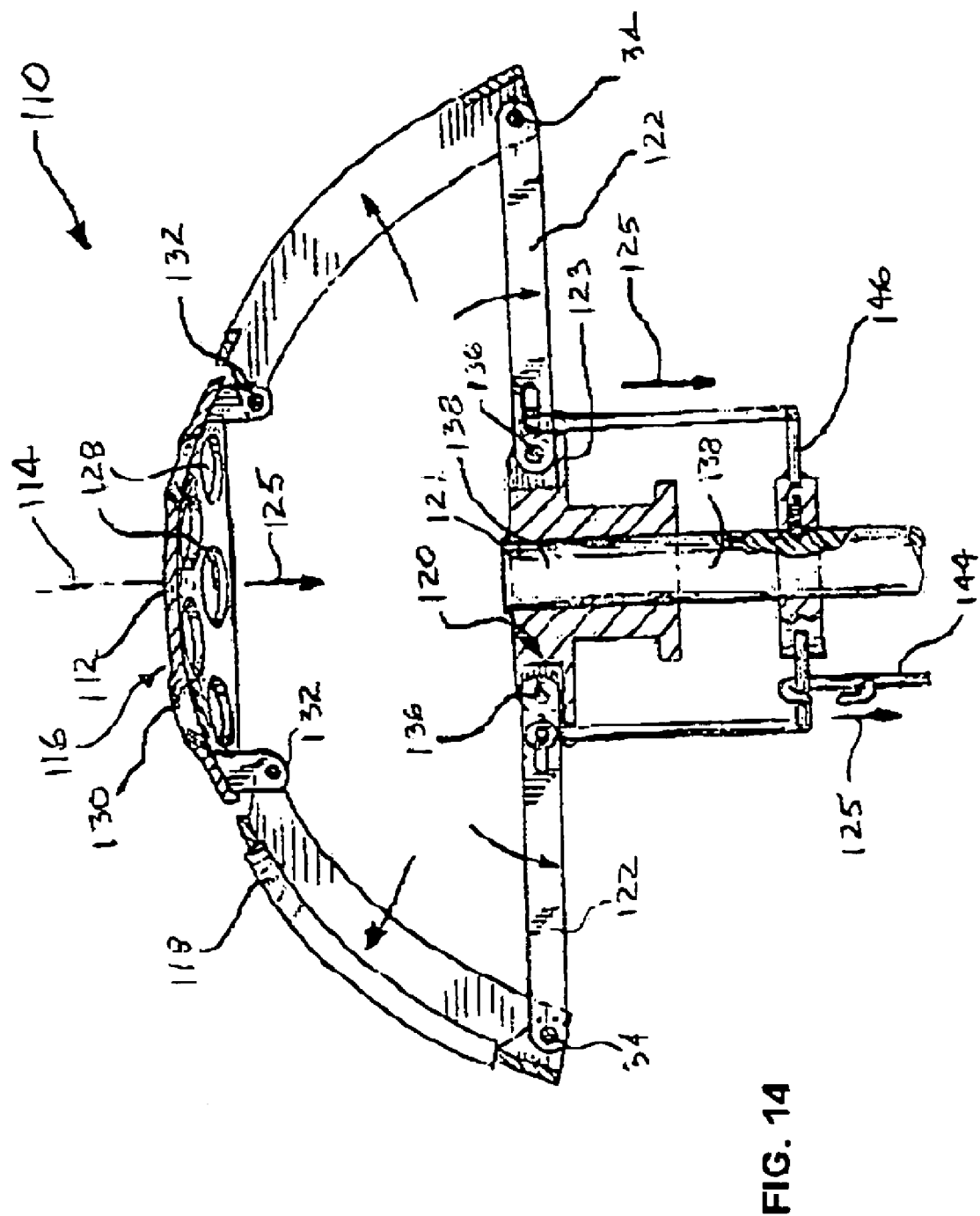
FIG. 14 is a sequential view of FIGS. 10 and 12, showing the cutting members (i.e., blades) locked in a state of full radial expansion for reaming a bone socket.
Figure 15:
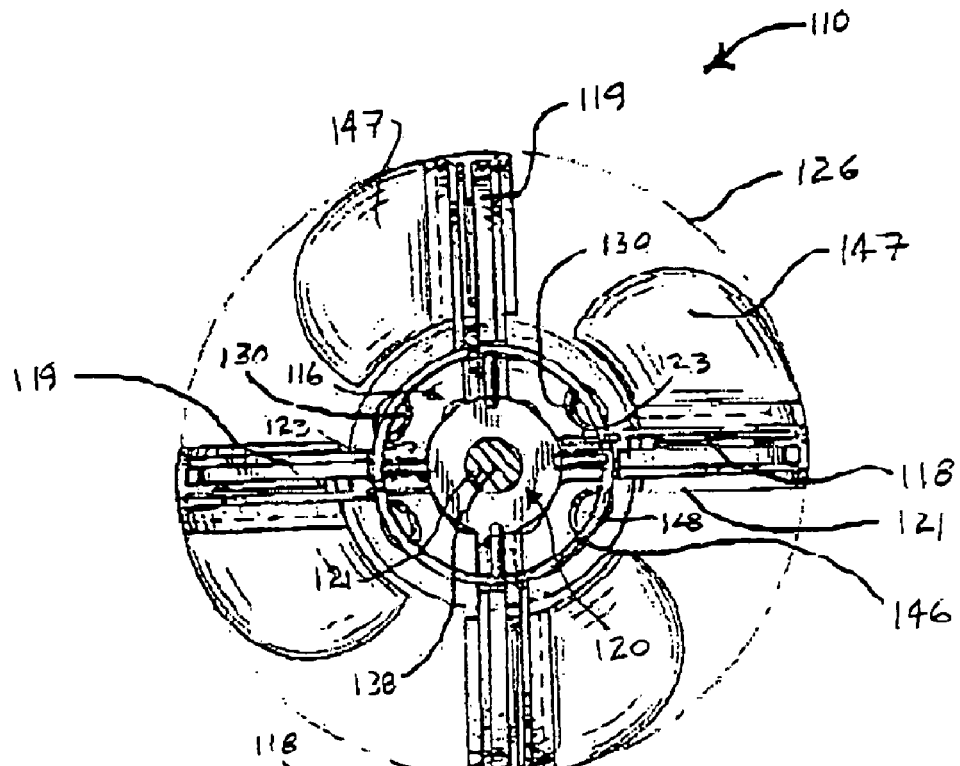
FIG. 15 is a bottom view of FIG. 9.
Figure 16:
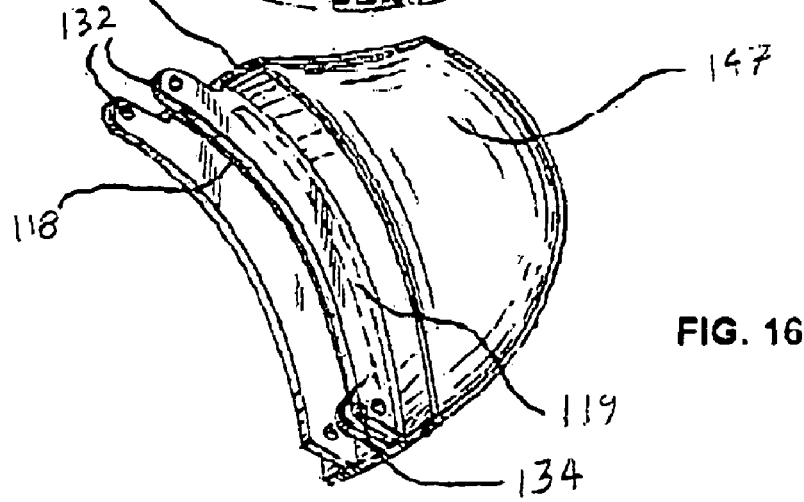
FIG. 16 is a partial view of a representative bladed cutting member of FIG. 9, showing fins for aiding in the collection of debris.

Referring to FIGS. 1-16 a surgical reamer for cutting a bone socket, preferably an acetabular reamer is generally shown at 10, 110 according to one aspect of the present invention. The reamer 10, 110 defines an apex 12, 112 and is rotatable about a drive axis 14, 114. The reamer has a support portion 16, 116 adjacent apex 12, 112 and a plurality of cutting members 18, 118 each pivotally mounted on the support portion as further described below. A hub structure 20, 120 including a sleeve portion 21, 121 is movable along axis 14, 114 toward and away from apex 12, 112. A plurality of spokes 22, 122 operatively connect cutting members 18, 118 and hub 20, 120, respectively. Actuation of hub 20, 120 by its movement along drive axis 14, 114 away from apex 12, 112 (arrow 24, 124) radially collapses spokes 22, 122 causing cutting members 18, 118 (ergo reamer 10, 110) to assume a less invasive insertion profile during passage of reamer 10, 110 through a surgical incision (not shown). Alternately, movement of huh 20, 120 it the opposite direction (arrow 25, 125) toward apex 12, 112 actuates the hub to radially expand spokes 22, 122 causing cutting members 18, 118 to assume a larger, cutting profile (indicated in phantom at 26, 126) while reaming a bone socket (not shown). Hub 20, 120 has a shoulder 23, 123 that limits radial expansion of spokes 22, 122 in the expanded state (FIGS. 6 and 14).

Preferably, support portion 16, 116 defines a hollow concave domed shape, more preferably formed with discrete open cutting sites 28, 128 having raised teeth 30, 130 allowing for passage of debris while reaming the bone socket then collection of the debris within the domed support portion. Support portion 16, 116 may further be provided with a centering tooth or pilot drill (not shown) at apex 12, 112 to aid in positioning the reamer within the bone socket while reaming.

Preferably, the cutting members are pivotally connected to the domed portion by a first plurality of hinges 32, 132 and to spokes 22, 122 by a second plurality of hinges 34, 134, the spokes being in turn connected to hub 20, 120 by a third plurality of hinges 36, 136. Hub 20, 120 is mounted on a shaft 38, 138 in either a fixed or slidable manner as will be separately described below in conjunction with the preferred embodiments of the invention.

Preferably, reamer 10, 110 is equipped with a suitable locking mechanism, e.g., a spring-loaded button (not shown) of a type operable manually by the surgeon as will be appreciated by those skilled in the art, to maintain hub 20, 120 axially fixed when the reamer is in an expanded state for reaming or in a collapsed state for passage through the incision.

Referring to FIGS. 1-8, there is provided a surgical reamer 10 for cutting a bone socket according to a preferred embodiment of the present invention, defining a drive axis 12 and an apex 14. Reamer 10 has a hollow, concave domed support portion 16 and a plurality of cutting panels 18 each supported about the domed portion by the hinges 32. Pluralities of open cutting sites 40 are located on the panels, respectively, including raised teeth 42 at the cutting sites, for passage of debris. Hub 20 of reamer 10 slides along shaft 38 coincident with axis 14 toward and away from apex 12, with spokes 22 extending between and interconnecting the cutting panels 18 and the hub, respectively. Actuation of hub 20 by axial sliding movement along shaft 38 radially collapses spokes 22 causing cutting panels 18 to assume a less invasive insertion profile during passage of the reamer 10 through a surgical incision, and then radially expands the cutting panels to assume a larger, cutting profile 26 while reaming the bone socket. In this embodiment, the shaft 38 extends axially into the underside of the domed portion 16 and may be terminally affixed therein as shown, due to the slidable coupling of the hub 20 to the shaft. A pin 39 that abuts the hub 20 when the reamer 10 is in a fully expanded state for reaming the bone socket limits axial movement of the shaft 38 toward the apex 12.

Referring to FIGS. 9-16, there is provided a surgical reamer 110 for cutting a bone socket according to another preferred embodiment of the present invention. Reamer 110 is rotatable about the drive axis 112, with the apex 114 having a plurality of bladed cutting members 118 that open into slits 119, respectively supported about the domed portion 116 by the first plurality of hinges 132. The pluralities of spokes 122 extend between and interconnect the cutting blades 118 and the hub 120, respectively. The spokes 122 are actuated by axial movement of the shaft 138, which in this embodiment (unlike the embodiment of FIGS. 1-8) is affixed to the hub 120 so that both the shaft and the hub move together. Movement of hub 120 and shaft 138 toward apex 112 radially collapses spokes 122 causing the cutting blades 118 to assume a less invasive insertion profile for passage through a surgical incision. Alternately, movement of hub 120 and shaft 138 toward apex 112 radially expands spokes 122 causing the bladed cutting members to assume the cutting profile 126 for reaming the bone socket. The reamer defines an internal cavity for collection of debris. It should be noted that the shaft 138 is not terminally affixed to the underside of the domed portion 116, compared with the above-mentioned embodiment of FIGS. 1-8, however it will be appreciated that the hub 120 could be slidably coupled as in FIGS. 1-8. Vice versa, the hub 20 and shaft 38 of FIGS. 1-8 could be relatively fixed as in FIGS. 9-16. It will be further appreciated that the direction of actuation could be reversed in either of the above embodiments, i.e., hub 20, 120 could be designed to radially expand cutting members 18, 118 when moved away from apex 12, 112 and collapse the cutting members when the hub is moved toward the apex, although this variation is not illustrated herein. In any case, a grasping tool 44, 144 facilitates movement of the hub 20, 120, as shown in FIGS. 1-6 and 10-14, by hooking onto a ringed cage 46, 146 associated with the hub. In FIGS. 9-16 there are shown fins 147 appended to the cutting members 118 to aid in the collection of debris.

According to a second aspect of the present invention, there is provided a surgical kit for cutting a bone socket. The kit includes a plurality of reamers 10, 110 of the type described above in conjunction with FIGS. 1-16, in an array of sizes corresponding to the needs of individual patients. Each size of reamer 10, 110 preferably has a hollow, concave domed portion 16, 116 defining an apex 12, 112 and a drive axis 14, 114, preferably with a shaft extending along the drive axis. Each reamer 10, 110, has a plurality of cutting members 18, 118 pivotally supported by the domed portion 16, 116, a hub structure 20, 120 including a sleeve portion 21, 121 movable along axis 14, 114 toward and away from the apex 12, 112 and a plurality of spokes 22, 122 extending between the cutting members and the hub, respectively. Actuation of hub 20, 120 radially collapses spokes 22, 122 causing cutting members 18, 118 to assume a less invasive insertion profile during passage of reamer 10, 110 through a surgical incision, and then radially expands the spokes causing the cutting members to assume a larger, cutting profile 26, 126 while reaming the bone socket. Hub 20, 120 has a shoulder 23, 123 that limits motion of spokes 22, 122 in the fully expanded state. The kit further includes an instrument handle (not shown) for holding the reamer 10, 110, including a quick-disconnect coupling for engaging and disengaging the reamer with a source of rotary power. A suitable instrument holder is described in U.S. Pat.

No. 5,658,290, the entire contents of which are incorporated by reference herein and relied-upon.

According to a third aspect of the present invention, there is provided a surgical method for cutting a bone socket in a patient. The method includes the steps of: providing a reamer 10, 110 defining an apex 12, 112 and a drive axis 14, 114, the reamer having a (preferably domed) support portion 16, 116 adjacent the apex, a plurality of cutting members 18, 118 each pivotally mounted on the support portion, a hub 20, 120 movable along the drive axis toward and away from the apex and collapsible spokes 22, 122 operatively connecting the cutting members and the hub, respectively. Another step includes providing a manual holder (not shown) coupled to a source of rotary power and releasably connecting the reamer 10, 110 to the holder. Another step includes manually actuating the hub 20, 120 to radially collapse the spokes 22, 122 causing the cutting members 18, 118 to assume a less invasive insertion profile and passing the reamer 10, 110 through a surgical incision thence to the bone socket. Another step includes actuating the hub 20, 120 to radially expand the spokes 22, 122 causing the cutting members 18, 118 to assume a cutting profile 26, 126 larger than the insertion profile in the bone socket, then reaming the bone socket and collecting the surgical debris within the reamer. Another step includes actuating the huh 20, 120 to radially collapse the spokes 22, 122 causing the cutting members 18, 118 to assume the smaller, less invasive insertion profile and thence removing the reamer with its collected debris back through the incision.

Each of the above-listed aspects and preferred embodiments of the present invention is most preferably an acetabular reamer 10, 110. It is further preferred that reamer 10, 110 has a locking mechanism (not shown) the alternately maintains cutting members 18, 118 in a radially collapsed insertion profile and in a larger, radially expanded cutting profile 26, 126 as assumed in the description elucidated above.

While one or more preferred embodiments of the present invention have been described, it should be understood that various changes, adaptations and modifications might be made without departing from the spirit of the invention and the scope of the appended claims.

The invention claimed is:

1. A surgical reamer for cutting a bone socket, defining a drive axis, an apex and comprising: a support portion aligned with the drive axis; a plurality of cutting members each mounted on the support portion; and a plurality of spokes operatively connected to the cutting members, wherein actuation of the spokes radially collapses the cutting members causing the reamer to assume an insertion profile during passage through a surgical incision, and then expands the reamer to assume a larger, cutting profile while reaming the bone socket, wherein further the cutting members are pivotally connected to the support portion by hinges wherein the support portion has discrete cutting sites, the support portion further defining a hollow concave domed shape to position the reamer in the bone socket and collect surgical debris during reaming for removal through the incision.

2. The reamer of claim 1 further comprising a releasable locking mechanism that alternately maintains the cutting members in a radially expanded state for reaming or in a collapsed state for passage through the incision.

3. A surgical kit for cutting a bone socket comprising: (a) a plurality of reamers according to claim 1, the reamers including an array of sizes corresponding to the needs of individual patients; and (b) a manual holder for grasping one of the reamers, including a quick-disconnect coupling for engaging and disengaging the reamer with a source of rotary power.

4. The kit of claim 3 wherein the reamer has cutting members which form solid panels having discrete cutting sites with raised teeth.

5. The kit of claim 3 wherein the reamer has cutting members which comprise arcuate blades, including appended fins for collection of debris.

6. The kit of claim 3 wherein the reamer has cutting members which are pivotally connected to the support portion by hinges.

7. The kit of claim 3 wherein the reamer has a support portion which has discrete cutting sites with raised teeth, the support portion further defining a hollow concave domed shape to position the reamer in the bone socket and collect surgical debris during reaming for removal through the incision.

8. The kit of claim 3, the reamer further comprising a releasable locking mechanism that alternately maintains the cutting members in a radially expanded state for reaming or in a collapsed state for passage through the incision.

9. A surgical method for cutting a bone socket in a patient, comprising the steps of: (a) providing the reamer of claim 1; (b) providing a manual holder coupled to a source of rotary power and releasably connecting the reamer to the holder; (c) actuating the spokes and radially collapsing the cutting members causing the reamer to assume an insertion profile and passing the reamer through a surgical incision thence to the bone socket; (d) actuating the spokes and radially expanding the cutting members causing the reamer to assume a cutting profile larger than the insertion profile, in the bone socket; (e) reaming the bone socket and collecting the surgical debris within the reamer; and (f) actuating the spokes and radially collapsing the cutting members causing the reamer to assume the smaller, insertion profile and thence removing the reamer with collected debris back out through the incision.

10. The surgical method of claim 9 wherein the cutting members of step (a) form solid panels having discrete cutting sites with raised teeth.

11. The surgical method of claim 9 wherein the cutting members of step (a) comprise arcuate blades including appended fins for collection of debris.

12. The surgical method of claim 9 wherein the support portion of step (a) includes discrete open cutting sites with raised teeth for passage of debris.

13. The surgical method of claim 9 wherein the support portion of step (a) defines a hollow concave domed shape to position the reamer in the bone socket arid collect surgical debris during reaming for removal through the incision.

14. A surgical reamer for cutting a bone socket comprising: a hollow, concave domed portion defining a drive axis and an apex; a shaft extending along the drive axis for imparting rotary motion to the reamer; a plurality of cutting panels each hingedly supported by the domed portion; a plurality of open cutting sites located on the panels, including raised teeth at the cutting sites, for passage of debris; a hub structure including a sleeve portion movable along the axis toward and away from the apex; and a plurality of spokes operatively connecting the cutting panels and the hub structure, respectively, wherein actuation of the sleeve portion radially collapses the spokes causing the cutting panels to assume an insertion profile during passage of the reamer through a surgical incision, and then radially expands the cutting panels to assume a larger, cutting profile while reaming the bone socket.

15. The reamer of claim 14 wherein the sleeve is slidably coupled to the shaft.

16. The reamer of claim 14 wherein the sleeve is affixed to the shaft and is movable with the shaft toward and away from the apex.

17. A surgical method for cutting a bone socket in a patient, comprising the steps of: (a) providing the reamer of claim 14; (b) providing a manual holder coupled to a source of rotary power and releasably connecting the reamer to the holder; (c) actuating the spokes and radially collapsing the cutting members causing the reamer to assume an insertion profile and passing the reamer through a surgical incision thence to the bone socket; (d) actuating the spokes and radially expanding the cutting members causing the reamer to assume a cutting profile larger than the insertion profile, in the bone socket; (e) reaming the bone socket and collecting the surgical debris within the reamer; and (f) actuating the spokes and radially collapsing the cutting members causing the reamer to assume the smaller, insertion profile and thence removing the reamer with collected debris back out through the incision.

18. The surgical method of claim 17 wherein the cutting members of step (a) form solid panels having discrete cutting sites with raised teeth.

19. The surgical method of claim 17 wherein the cutting members of step (a) comprise arcuate blades including appended fins for collection of debris.

20. The surgical method of claim 17 wherein the support portion of step (a) further defining a hollow concave domed shape to position the reamer in the bone socket and collect surgical debris during reaming for removal through the incision.

21. A surgical reamer for cutting a bone socket comprising: a hollow, concave domed portion defining a drive axis and an apex; a shaft extending along the drive axis; a plurality of cutting blades each hingedly supported by the domed portion; a plurality of fins respectively appended to the cutting blades, aiding in collection of debris; a hub structure including a sleeve portion movable along the axis toward and away from the apex; and a plurality of spokes operatively connecting the cutting blades and the hub structure, respectively, wherein actuation of the sleeve portion radially collapses the spokes causing the cutting blades to assume an insertion profile during passage of the reamer through a surgical incision, and then radially expands the cutting blades to assume a larger, cutting profile while reaming the bone socket.

22. The reamer of claim 21 wherein the sleeve is slidably coupled to the shaft.

23. The reamer of claim 21 wherein the sleeve is affixed to the shaft and is movable with the shaft toward and away from the apex.

* * * * *

UNITED STATES PATENT AND TRADEMARK OFFICE
CERTIFICATE OF CORRECTION

PATENT NO. : 7,632,276 B2  Page 1 of 1
APPLICATION NO. : 10/902692
DATED : December 15, 2009
INVENTOR(S) : Fishbein It is certified that error appears in the above-identified patent and that said Letters Patent is hereby corrected as shown below:

On the title page Item (73) Assignee, Delete "Greatbatch Medical S.A." and insert Item (73) Assignee --Mira Precision Surgical Instruments, Inc.--

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,632,276 B2 | Page 1 of 1 |
| APPLICATION NO. | : 10/902692 | |
| DATED | : December 15, 2009 | |
| INVENTOR(S) | : Meyer Fishbein | |

It is certified that error appears in the above-identified patent and that said Letters Patent is hereby corrected as shown below:

Column 8, line 46 - replace the phrase "position the reamer in the bone socket arid collect surgical" with "position the reamer in the bone socket and collect surgical".

Signed and Sealed this
Second Day of October, 2012

David J. Kappos
*Director of the United States Patent and Trademark Office*